United States Patent
Bittner et al.

(10) Patent No.: US 9,346,061 B2
(45) Date of Patent: May 24, 2016

(54) DIAMINE COMPOUNDS AND THEIR USE FOR INVERSE FROTH FLOTATION OF SILICATE FROM IRON ORE

(75) Inventors: Christian Bittner, Bensheim (DE); Joerg Nieberle, Wachenheim (DE); Bernhard Ulrich von Vacano, Mannheim (DE); Alexsandro Berger, Rosenheim (DE); Roland Boehn, Maxdorf (DE); Guenter Oetter, Frankenthal (DE)

(73) Assignee: BASF SE, Ludwigshafen (DE)

( * ) Notice: Subject to any disclaimer, the term of this patent is extended or adjusted under 35 U.S.C. 154(b) by 349 days.

(21) Appl. No.: 14/111,187

(22) PCT Filed: Apr. 4, 2012

(86) PCT No.: PCT/EP2012/056123
§ 371 (c)(1),
(2), (4) Date: Oct. 11, 2013

(87) PCT Pub. No.: WO2012/139939
PCT Pub. Date: Oct. 18, 2012

(65) Prior Publication Data
US 2014/0027354 A1   Jan. 30, 2014

Related U.S. Application Data

(60) Provisional application No. 61/474,759, filed on Apr. 13, 2011.

(30) Foreign Application Priority Data

Apr. 13, 2011   (EP) ..................... 11162203

(51) Int. Cl.
*B03D 1/02* (2006.01)
*B03D 1/01* (2006.01)
*C07C 233/18* (2006.01)
*C07C 233/17* (2006.01)
*B03D 1/004* (2006.01)

(52) U.S. Cl.
CPC ............... *B03D 1/01* (2013.01); *B03D 1/0043* (2013.01); *B03D 1/02* (2013.01); *C07C 233/17* (2013.01); *C07C 233/18* (2013.01); *B03D 2201/02* (2013.01); *B03D 2203/04* (2013.01)

(58) Field of Classification Search
None
See application file for complete search history.

(56) References Cited

U.S. PATENT DOCUMENTS

| | | | | |
|---|---|---|---|---|
| 2,356,821 | A * | 8/1944 | Christmann | B03D 1/01 209/166 |
| 2,569,417 | A | 9/1951 | Jayne et al. | |
| 2,629,494 | A | 2/1953 | Brown | |
| 3,179,250 | A | 4/1965 | Bunge et al. | |
| 3,363,758 | A * | 1/1968 | Cronberg | B03D 1/01 209/166 |
| 3,960,715 | A * | 6/1976 | Dicks | B03D 1/02 209/166 |
| 4,148,926 | A * | 4/1979 | Baker | C07D 307/68 426/321 |
| 4,319,987 | A | 3/1982 | Shaw et al. | |
| 4,422,928 | A | 12/1983 | McGlothlin et al. | |
| 5,124,028 | A | 6/1992 | Klimpel et al. | |
| 6,076,682 | A | 6/2000 | Gustafsson et al. | |
| 2009/0114573 | A1 | 5/2009 | Pedain et al. | |
| 2009/0152174 | A1 | 6/2009 | Pedian et al. | |

FOREIGN PATENT DOCUMENTS

| | | |
|---|---|---|
| CA | 1100239 A | 4/1981 |
| GB | 578694 | 7/1946 |
| JP | H04-227077 A | 8/1992 |
| WO | WO 2008/077849 A1 | 7/2008 |

OTHER PUBLICATIONS

International Search Report and Written Opinion issued Aug. 6, 2012 in PCT/EP2012/056123.
International Preliminary Report on Patentability and Written Opinion issued Oct. 24, 2013 in PCT/EP2012/056123.
English Translation of Japanese Office Action JP 2014-504253. Drafting date Jan. 28, 2016, Dispatch Date Feb. 8, 2016, 10 pp.

* cited by examiner

*Primary Examiner* — Thomas M Lithgow
(74) *Attorney, Agent, or Firm* — Oblon, McClelland, Maier & Neustadt, L.L.P.

(57) ABSTRACT

The invention concerns a process for enriching an iron mineral from a silicate containing iron ore by inverse flotation comprising the addition of a collector or collector composition comprising at least one of the compounds of formulae $RC(O)N(Z-O-X-NH_2)_2$ (Ia); $RC(O)N(Z-O-X-NH_2)_2H^+ Y^-$ (Ib); in which X is an aliphatic alkylene group containing 2 to 6 carbon atoms; Z is an aliphatic alkylene group containing 2 to 6 carbon atoms; $Y^-$ is an anion; and R is a saturated or unsaturated, linear or branched, aliphatic or aromatic moiety having between 7 and 23 carbon atoms. The invention also relates to the novel compounds according to formulae (Ia) and (Ib), compositions comprising said compounds and the use of compounds and formulations as collectors for enriching of iron mineral.

20 Claims, No Drawings

DIAMINE COMPOUNDS AND THEIR USE FOR INVERSE FROTH FLOTATION OF SILICATE FROM IRON ORE

The present invention relates to a process for enriching an iron mineral from a silicate-containing iron ore by carrying out an inverse ore flotation process using alkyl amido ether diamines. The invention also relates to novel alkyl amido ether diamines and formulations containing the same.

Removal of $SiO_2$ from different ores by froth flotation and hydrophobic amines is a well known process and is described for example by S. R. Rao in *Surface Chemistry of Froth Flotation, Volume 1 and 2*, $2^{nd}$ edition, Kluwer Academic/Plenum Publishers, New York 2004. The negatively charged silicate can be hydrophobized using suitable amines. Injection of air in a flotation cell leads to formation of hydrophobic gas bubbles, which can transport the hydrophobized silicate particle to the top of the flotation cell. At the top a froth, which can be stabilized by a suitable frother, collects the silicate particles. Finally, the froth will be removed from the surface and the enriched mineral is left at the bottom of the flotation cell.

In the case of iron ore, pure material is necessary to make high quality steel. Therefore the iron mineral can be enriched from a silicate-containing iron ore by inverse flotation. This kind of froth is carried out in the presence of a depressing agent for the iron mineral and collecting agent, which can contain hydrophobic amines, for instance alkyl ether amines and/or alkyl ether diamines.

In U.S. Pat. No. 2,629,494 (Attapulgus Minerals+Chemicals Corp., publication date 24 Feb. 1953) protonated hydrophobic amines like tetradecylamine acetate are described to remove silicate from iron oxide in the presence of starch as depressing agent.

U.S. Pat. No. 3,363,758 (Ashland Oil and Refining Company, publication date 16 Jan. 1968) relates to a froth flotation process for separating silica from an ore employing a water dispersible aliphatic ether diamine of the formula R—O—CH2CH(R")CH2NHCH2CH(R")CH2-NH2 in which R is an aliphatic radical having between one and 13 carbon atoms and R" is a hydrogen atom or a methyl group.

In CA1100239 (Akzona, Inc., publication date 28 Apr. 1981) alkyl ether diamines of the structure alkoxy —$CH_2CH_2CH_2$—NH—$CH_2CH_2CH_2$—$NH_2$ for removal of silicate from iron ore were described. Alkoxy unit should contain 6 to 22 carbon atoms and could be linear or branched. The disadvantage of linear alkoxy moieties is that the collector starts to crystallize with time. Additional solvent or a heating unit would be necessary to enable a liquid dosage.

Exxon Research and Engineering Co described in U.S. Pat. No. 4,319,987 (publication date 16 Mar. 1982) the use of alkoxy —$CH_2CH_2CH_2$—$NH_2$ for removal of silicate from iron ore. Alkoxy unit should contain 8-10 carbon atoms and should be branched.

U.S. Pat. No. 4,422,928 (Exxon Research and Engineering, publication date 27 Dec. 1983) reveals a froth flotation process for separating silica from iron ore employing a liquid aliphatic ether amine of the formula R—O—($R^1$—O)$_z$—$CH_2$—$CH_2$—$CH_2$—$NH_2$ in which R is an aliphatic methyl branched radical having nine carbon atoms, $R_1$ is ethyl or propyl and z is an integer of from zero to 10.

In U.S. Pat. No. 6,076,682 (AKZO NOBEL NV, publication date 20 Jun. 2000) combinations out of ether amines and ether polyamines for inverse iron ore flotation were described. Especially structures alkoxy —$CH_2CH_2CH_2$—$NH_2$ with alkoxy consisting out of 8 to 12 carbon atoms and alkoxy —$CH_2CH_2CH_2$—NH—$CH_2CH_2CH_2$—$NH_2$ with alkoxy consisting out of 8 to 14 carbon atoms were preferred.

WO 2008/077849 (AKZO NOBEL NV, publication date 3 Jul. 2008) describes a collecting composition for use in enriching an iron mineral from a silicate containing iron or containing coarse silicates having a $K_{80}$ value of at least 110 μm by reverse flotation of the ore. The composition contains a mixture of at least one diamine of the formula $R^1$O-A-NH $(CH_2)_n$NH2, in which $R^1$ is a straight or branched hydrocarbyl group which 12 to 15 carbon atoms, A is a group —$CH_2CHXCH_2$—, in which X is hydrogen or a hydroxyl group; at least one amine of the formula $R^2(O-A)_x$-NH2, in which $R^2$ is a straight or branched hydrocarbyl group with 12 to 24 carbon atoms, x=0 or 1, and A is as defined before; and at least one diamine of the formula $R^3(O-A)_y$-$NH(CH_2)_n$NH_2$, in which $R^3$ is a straight or branched hydrocarbyl group with 16 to 24 carbon atoms, y=0 or 1, and A is as defined before. Included in the lists of possible groups for each of $R^1$ and $R^2$ is methyl branched C13 alkyl (isotridecyl).

Despite a significant number of proposed structures in inverse iron ore flotation more selective compounds are needed because quality of ore has been decreasing. With higher $SiO_2$ content in the ore a selective removal of silicate is more difficult than in the past with ores of higher quality. Loss of iron ore in the flotation process should be avoided and silicate content should be decreased to a very low level especially for direct reduction processes (DRI-pellets). Therefore it is an objective of the present invention to find collectors which are useful for enriching an iron mineral that achieve this objective, especially for difficult iron ores containing high silicate content.). It would be desirable to provide suitable flotation collectors and processes of selective removal of silicate from iron ore which overcome the aforementioned disadvantages. Furthermore, it would be desirable to provide flotation collectors which can be conveniently employed in flotation processes. It is particularly desirable for such floatation collectors to be in a liquid form.

According to the present invention we provide a process for enriching an iron mineral from a silicate containing iron ore by inverse flotation comprising the addition of a collector or collector composition comprising at least one of the compounds of formulae

$$RC(O)N(Z-O-X-NH_2)_2 \quad (Ia);$$

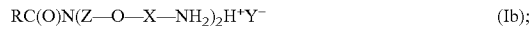
$$RC(O)N(Z-O-X-NH_2)_2H^+Y^- \quad (Ib);$$

in which

X is an aliphatic alkylene group containing 2 to 6 carbon atoms;

Z is an aliphatic alkylene group containing 2 to 6 carbon atoms;

$Y^-$ is an anion; and

R is a saturated or unsaturated, linear or branched, aliphatic or aromatic hydrocarbyl moiety having between 7 and 23 carbon atoms.

The X and Z aliphatic alkylene groups may each independently be linear or branched when containing 3 to 6 carbon atoms.

In the process these compounds have been found to exhibit an improved selective removal of silicate from the iron ore prepared commercially available or other known alkyl ether amines or alkyl ether diamines. Such known products result in a high residual content of silicate and/or loss of iron in providing the enriched iron mineral.

In accordance with the present invention either of the compounds of formulae (Ia) or (Ib) provide improved results in enriching the iron material. Preference may be given to using a combination of these compounds. For instance an alkyl ether amine compound (Ia) may be used in combination with a protonated alkyl ether amine compound (Ib). Thus these compounds or combinations thereof used in the process according to the present invention show a much better selective removal of silicate compared to the commercially available or other known alkyl ether amines or alkyl ether diamines.

In a preferred form X is an aliphatic alkylene group containing between 2 and 4 carbon atoms and especially three carbon atoms. It particularly preferred alkylene group has the structure —$CH_2CH_2CH_2$—.

Similarly in a preferred form Z is an aliphatic alkylene group containing between 2 and 4 carbon atoms and especially two carbon atoms. It particularly preferred alkylene group has the structure —$CH_2CH_2$—.

The anion $Y^-$ may be any suitable anion including a carboxylate, sulphate, sulphonate, chloride, bromide, iodide, fluoride, nitrate, phosphate etc. Preferably the anion is a carboxylate particularly an aliphatic or olefinic carboxylate of between 1 and 6 carbon atoms. More preferably the carboxylate is an aliphatic carboxylate of between 1 and 3 carbon atoms such as $HCO_2^-$, $CH_3CO_2^-$, $CH_3CH_2CO_2^-$. $CH_3CO_2^-$ is especially preferred.

The R group of compounds of formulae (Ia) and/or (Ib) is a saturated or unsaturated, linear or branched, aliphatic or aromatic hydrocarbyl group with between 7 and 23 carbon atoms. Preferably the hydrocarbyl group contains between 11 and 21 carbon atoms, and more preferably between 12 and 20 carbon atoms, for instance between 13 and 19 carbon atoms, such as 14, 15 16, 17 or 18 carbon atoms. It is preferred that the hydrocarbyl group is aliphatic. It is also preferred that the hydrocarbyl is unsaturated. Particularly preferred compounds include compounds in which the R group is an unsaturated aliphatic hydrocarbyl group with between 16 and 18 carbon atoms, especially 17 carbon atoms.

In one preferred form of the present invention either of the compounds of formulae (Ia) or (Ib) or combination thereof may be used in conjunction with at least one of compounds of formulae:

R'O—$CH_2CH_2CH_2$—$NH_2$ (IIa)

R'O—$CH_2CH_2CH_2$—$NH_3^+Y^-$ (IIb)

wherein R' is a branched hydrocarbyl group of between 8 and 18 carbon atoms, preferably between 10 and 15 carbon atoms, and Y is independently selected from the aforementioned definition.

In one alternative preferred form of the present invention either of the compounds of formulae (Ia) or (Ib) or combination thereof may be used in conjunction with at least one of compounds of formulae:

R'O—$CH_2CH_2CH_2$—NH—$CH_2CH_2CH_2$—$NH_2$ (IIIa)

R'O—$CH_2CH_2CH_2$—NH—$CH_2CH_2CH_2$—$NH_3^+Y^-$ (IIIb)

wherein R' and Y are each independently selected from the aforementioned definitions.

It may also be desirable to employ either of the compounds of formulae (Ia) or (Ib) or combination thereof in conjunction with compounds (IIa) and/or (IIb) and also compounds (IIIa) and/or (IIIb).

The invention also relates to novel compounds of formulae

RC(O)N(Z—O—X—$NH_2$)$_2$ (Ia);

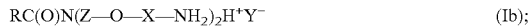

RC(O)N(Z—O—X—$NH_2$)$_2$H$^+$Y$^-$ (Ib);

in which X, Y, Z and R are each independently selected from the aforementioned definitions.

Compounds of formula (Ia) may be prepared by firstly reacting carboxylic acid ester RC(O)—OM with a dialkanolamine HN(Z—OH)$_2$ to provide the corresponding alkyl amido dialkanol RC(O)—N(Z—OH)$_2$ in which R and Z are as defined previously and M is typically a lower alkyl such as methyl or ethyl and for example represents the alkyl group of an ester derived from the alcohol component.

The carboxylic acid ester may be obtained commercially. For instance it may be a mixture of dodecanoic acid methyl ester and tetradecanoic acid methyl ester in an outrage weight ratio of approximately 70:30 obtained from Cognis. Alternatively, it may be the methyl ester of oleic acid, linoleic acid or linolenic acid also available from a variety of commercial sources. It may be obtained from Aldrich. The dialkanolamine may for instance be diethanolamine, dipropanolamine, dibutanolamine, dipentanolamine or dihexanolamine including all of the respective isomers.

It may be desirable to prepare the alkyl amido dialkanol by reacting the carboxylic acid ester with the dialkanolamine in equal molar proportions but usually it may be preferable to employ a molar excess of the dialkanolamine. Typically the ratio of ester to dialkanolamine will be in the range of 1.25:1 to 1:7, preferably 1:1 to 1:5.

The two components desirably may be combined at an elevated temperature, for instance at least 50° C. and up to 85° C., for instance between 70° C. and 80° C. Desirably the reaction should be carried out at an elevated temperature of at least 100° C. and usually higher, for instance up to 150° C., suitably between 110° C. and 130° C. The reaction product alkyl amido dialkanol should form and desirably the byproduct alcohol should be distilled off. In order to facilitate removal of the byproduct it is therefore desirable that the alcohol has a relatively low boiling point, and preferably is methanol. Consequently, the preferred carboxylic acid ester would tend to be the methyl ester. During the course of the reaction it may be desirable to add additional dialkanolamine in order to improve the conversion rate. This may be done at the same temperature as the main reaction or alternatively at a slightly lower temperature for instance between 75° C. and 120° C., typically at least 85° C. The total reaction time may be between 60 minutes and 360 minutes, for instance between 90 minutes and 180 minutes.

Once the reaction is complete the alkyl amido dialkanol may be separated from the reaction mixture at an ambient temperature, for instance between 15° and 35° C. Typically a suitable solvent may be employed, such as an ether, for instance tert-butyl methyl ether. A suitable acid may then be added to this mixture, for instance diluted acetic acid (typically 1% acetic acid in water). The solvent may be removed from the mixture by evaporation, preferably under vacuum or reduced pressure. The product may then be combined with a suitable solvent and base. It may be desirable employ a base and an aprotic solvent such as tetrahydrofuran. Typically the base may be an alkali metal alkoxide, preferably an alkali metal ethoxide or alkali metal methoxide, especially sodium methoxide. The mixture may then be combined with a suitable resin such as Ambosol, which is a polysulfonic acid, and then after stirring for a period, for instance up to 60 minutes the product may be separated by filtering.

Alternatively the alkyl amido dialkanol can be made by reaction of carboxylic acid with the dialkanol amine. Reaction can take place between 80 and 160° C. Reaction water can be distilled off or removed under vacuum (15-100 mbar).

In the next step the alkyl amido dialkanol may be reacted with an ethylenically unsaturated nitrile, containing between 3 and 6 carbon atoms, to provide an alkyl amido di(alkyl ether nitrile). Suitable ethylenically unsaturated nitriles include acrylonitrile, methacrylonitrile, ethacrylonitrile, 2-n-propylacrylonitrile, 2-iso-propylacrylonitrile, 2-methyl-1-butenenitrile, 3-methyl-1-butenenitrile, 2,2-dimethyl-1-butenenitrile, 2,3-dimethyl-1-butenenitrile, 2-ethyl-1-butenenitrile, 3-ethyl-1-butenenitrile, 2-methyl-1-butenenitrile, 3-methyl-1-butenenitrile, 2,3-dimethyl-1-butenenitrile, 2-ethyl-1-butenenitrile, 1-pentenenitrile, 2-methyl-1-pentenenitrile, 3-methyl-1-pentenenitrile, 4-methyl-1-pentenenitrile, Preferably the ethylenically unsaturated nitrile would contain three carbon atoms i.e. acrylonitrile. It may be desirable to carry out this step in the presence of a base and a polar solvent. Typically the base may be an alkali metal alkoxide, preferably an alkali metal ethoxide or alkali metal methoxide, especially sodium methoxide. The ethylenically unsaturated nitrile may be added in an amount equivalent to twice the molar quantity of the alkyl amido dialkanol. Usually the ethylenically unsaturated nitrile should be added in a stoichiometric excess to this 2:1 ratio in order to ensure that all of the alkyl amido dialkanol is reacted. Often the molar ratio of the ethylenically unsaturated nitrile to the alkyl amido dialkanol can be above 2:1 and up to 10:1, preferably from 2.5:1 to 5:1, more desirably between 2:1 and 4:1.

It may be desirable to combine the ethylenically unsaturated nitrile with the alkyl amido dialkanol already containing the base over a period of between 5 minutes and 75 minutes or more, preferably between 30 minutes and 60 minutes. It may be desirable to control the rate of combining the nitrile with the alcohol in order to ensure an optimum temperature is achieved. The reaction temperature may be between 10° C. and 60° C. It may be desirable to control the temperature such that it does not exceed 50° C. The reaction time may be over a period of at least 5 minutes and as long as 24 hours. Typically the reaction will be at least 5 minutes and often as much as 10 hours or more. At the end of the reaction it may be desirable to remove the excess ethylenically unsaturated nitrile by conventional means, for example by evaporation under vacuum. Suitably the ethylenically a saturated nitrile may be removed under vacuum with a reduced pressure of between 15 mbar and 100 mbar at an elevated temperature of between 30° C. and 60° C. for a period of between 30 minutes and 180 minutes and optionally at an increased temperature of at least 65° C. and up to 85° C. Optionally it may be desirable to use a resin to remove any trace amounts of the nitrile. Desirably the resulting alkyl amido di-(alkyl ether nitrile) should have a purity of at least 90% and often at least 95%.

In a third step of the process the nitrile group of the alkyl amido di-(alkyl ether nitrile) of step two is reduced to the corresponding diamine. This can be achieved by any conventional process for the reduction of nitriles to amines. Desirably the alkyl ether nitrile should be reacted with hydrogen in the presence of a suitable catalyst. An example of a suitable catalyst includes Raney-Cobalt. This may be carried out in the presence of a suitable aprotic solvent such as tetrahydrofuran.

Typically the reaction may be carried out at elevated temperatures, for instance at least 80° C., desirably at least 90° C., and possibly up to 140° C. or more. Preferably the reaction would be carried out at temperatures of between 100° C. and 130° C. In addition to elevated temperatures it may often be desirable to carry out process under increased pressure usually of at least 40 bar or more, for instance at least 45 bar. It may often be desirable to increase the pressure to even higher levels for instance up to 350 bar or higher, for instance between 250 bar and 300 bar. At the end of the reaction it may usually be desirable to remove the catalyst. This can be done by conventional filtration means.

Desirably the resulting alkyl amido di-(alkyl ether amine) should have a purity of at least 75%, more preferred at least 85% and often at least 89% or 90% or higher.

The compounds of formulae (Ib) may conveniently be prepared by addition of an acidic compound to the corresponding alkyl ether amine of formulae (Ia). The acidic compound will protonate the amine groups and then the negatively charged acid radical will form the negatively charged $Y^-$ component. The acidic compound may be any suitable acid, for instance acids whose radicals are selected from the group consisting of carboxylate, sulphate, sulphonate, chloride, bromide, iodide, fluoride, nitrate, and phosphate. Preferably the acid is a carboxylic acid, particularly an aliphatic or olefinic carboxylic acid having between one and six carbon atoms. More preferably a carboxylic acid is an aliphatic carboxylic acid having between one and three carbon atoms i.e. formic acid, acetic acid or propionic acid. Acetic acid is preferred.

The acidic compound may be added in a 2:1 molar ratio to the alkyl amido di-(alkyl ether amine) compound of formula (Ia). It may be desirable to add a lesser amount of the acidic compound which will result in partial protonation and therefore result in a mixture of the protonated compound of formula (Ib) and the corresponding alkyl amido di-(alkyl ether amine) compound of formula (Ia). It may also be desirable to add a greater amount of the acidic compound resulting in a stoichiometric excess of the acidic compound. Typically the ratio of acidic compound to alkyl amido di-(alkyl ether amine) may be between 1:20 and 5:1, for instance between 1:18 and 1:1, such as 1:18 to 1:12 or alternatively between 1:5 and 1:1.

The acidic compound may be added over a period of time between one minute and 45 minutes to the alkyl amido di-(alkyl ether amine), for instance between five minutes and 30 minutes. The resulting compound of formulae (Ib) respectively desirably will form as a homogenous solution which will remain clear and liquid during storage.

Compounds of formula (IIa) may be prepared by firstly reacting an alcohol R'OH with acrylonitrile. It may be desirable to carry out this step in the presence of a base and a polar solvent. Typically the base may be an alkali metal alkoxide, preferably an alkali metal ethoxide or alkali metal methoxide, especially sodium methoxide. The acrylonitrite may be added in an equivalent molar quantity to the alcohol. Usually the acrylonitrile should be added in a stoichiometric excess in order to ensure that all of the alcohol is reacted. Often the molar ratio of the acrylonitrile to the alcohol can be above 1:1 and up to 10:1, preferably from 1.5:1 to 5:1, more desirably between 1:1 and 2:1.

The alcohol R'OH may be any branched alcohol or any linear fatty alcohol with between 8 and 18 carbon atoms. Branched alcohols R'OH are preferred. Branched alcohols R'OH may be obtained commercially by BASF, Exxon, Shell or DOW. Linear alcohols can be obtained by Cognis, Sasol or Shell.

It may be desirable to combine the acrylonitrile with the alcohol already containing the base over a period of between 5 minutes and 75 minutes or more, preferably between 30 minutes and 60 minutes. It may be desirable to control the rate of combining the nitrile with the alcohol in order to ensure an optimum temperature is achieved. The reaction temperature may be between 10° C. and 60° C. It may be desirable to control the temperature such that it does not exceed 50° C. The reaction time may be over a period of at least 10 minutes and as long as 24 hours. Typically the reaction will be at least 60 minutes and often as much as 10 hours or more. At the end of the reaction it may be desirable to remove the excess acrylonitrile by conventional means, for example by evaporation under vacuum. Suitably the acrylonitrile may be removed under vacuum with a reduced pressure of between 15 mbar and 100 mbar at an elevated temperature of between 30° C. and 60° C. for a period of between 30 minutes and 60 minutes and optionally at an increased temperature of at least 65° C. and up to 85° C. Optionally it may be desirable to use a resin to remove any trace amounts of the nitrile. Desirably the resulting alkyl ether nitrile should have a purity of at least 90% and often at least 95%.

In a second step of the process the nitrile group of the alkyl ether nitrile of step one is reduced to the corresponding amine. This can be achieved by any conventional process for the reduction of nitriles to amines. Desirably the alkyl ether nitrile should be reacted with hydrogen in the presence of a suitable catalyst. An example of a suitable catalyst includes Raney-Cobalt. This may be carried out in the presence of a suitable aprotic solvent such as tetrahydrofuran.

Typically the reaction may be carried out at elevated temperatures, for instance at least 80° C., desirably at least 90° C., and possibly up to 140° C. or more. Preferably the reaction would be carried out at temperatures of between 100° C. and 130° C. In addition to elevated temperatures it may often be desirable to carry out process under increased pressure usually of at least 40 bar or more, for instance at least 45 bar. It may often be desirable to increase the pressure to even higher levels for instance up to 350 bar or higher, for instance between 250 bar and 300 bar. At the end of the reaction it may usually be desirable to remove the catalyst. This can be done by conventional filtration means.

Desirably the resulting alkyl ether amine should have a purity of at least 85% and often at least 89% or 90% or higher.

In an alternative process for producing the aforementioned alkyl ether amine the respective alcohol can be reacted with a C2-6 alkylene oxide to produce the corresponding alkyl ether alcohol. In a first step an alcohol R'OH in which the R' group is as defined previously can suitably be reacted with 1 eq of alkylene oxide like ethylene oxide, propylene oxide, 1,-2-butylene oxide, 2,3-butylene oxide, 1,2-pentene oxide and/or 1,2-hexene oxide. Therefore alcohol R'OH is mixed with a base like sodium hydroxide, potassium hydroxide or cesium hydroxide or aqueous solution out of it and reaction water is removed under reduced vacuum (15 to 100 mbar) at elevated temperature (80-120° C.) for suitable time. This could last between 0.5 and 3 hours. Reaction vessel is then flushed several times with nitrogen and heated to 100-160° C. Alkylene oxide is added in such a way that reaction temperature does not exceed 180° C. Optionally base can be neutralized with an acid (for example acetic acid) and resulting salt can be removed by simple filtration. Reaction lead to a mixture of showing a molecular weight distribution with an average alkoxylation degree of 1. Alkoxylation reaction can also be catalyzed by amines like imidazol or tertiary amines or double metal catalysts. In a second step product from reaction before can be mixed with a suitable catalyst optionally in presence of an aprotic solvent like tetrahydrofurane. Reaction vessel is flushed several times with nitrogen in order to remove air. Afterwards ammonia (1-200 eq) and hydrogen (4-200 eq) are added up to a pressure of 50 bar. Reaction is heated under stirring to 200° C. Pressure should be kept below 280 bar. Further hydrogen is added (in case of pressure drop) and stirred over a period up to 24 h. Reaction is cooled to 40° C., gas is removed and vessel flushed several times with nitrogen. Catalyst can be removed by filtration and solvent can be removed under vacuum. Conversion of alcohol group into a primary amino group is at least 85% or even higher.

The compounds of formulae (IIb) may conveniently be prepared by addition of an acidic compound to the corresponding alkyl ether amine of formulae (IIa). The acid the compound will protonate the amine group and then the negatively charged acid radical will form the negatively charged $Y^-$ component. The acidic compound may be any suitable acid, for instance acids whose radicals are selected from the group consisting of carboxylate, sulphate, sulphonate, chloride, bromide, iodide, fluoride, nitrate, and phosphate. Preferably the acid is a carboxylic acid, particularly an aliphatic or olefinic carboxylic acid having between one and six carbon atoms. More preferably a carboxylic acid is an aliphatic carboxylic acid having between one and three carbon atoms i.e. formic acid, acetic acid or propionic acid. Acetic acid is preferred.

The acidic compound may be added in a molar equivalence to the alkyl ether amine compound of formula (IIa). It may be desirable to add a lesser amount of the acidic compound which will result in partial protonation and therefore result in a mixture of the protonated compound of formula (IIb) and the corresponding alkyl ether amine compound of formula (IIa). It may also be desirable to add a greater amount of the acidic compound resulting in a stoichiometric excess of the acidic compound. Typically the ratio of acidic compound to alkyl ether amine may be between 1:10 and 1.5:1, especially between 1:7 and 1:1.

The acidic compound may be added over a period of time between one minute and 45 minutes to the alkyl ether amine, for instance between five minutes and 30 minutes. The resulting compound of formulae (IIb) respectively desirably will form as a homogenous solution which will remain clear and liquid during storage.

The alkyl ether diamines of formulae (IIIa) may be synthesised by reacting the respective alkyl ether amine of formulae (IIa) with acrylonitrile.

The acrylonitrile may be added in an equivalent molar quantity to the alkyl ether amine. Usually the ethylenically unsaturated nitrile should be added in a stoichiometric excess in order to ensure that all of the alkyl ether amine is reacted. Often the molar ratio of the acrylonitrile to the amine can be above 1:1 and up to 10:1, preferably from 1.5:1 to 5:1, more desirably between 1:1 and 2:1.

It may be desirable to combine the acrylonitrile with the alkyl ether amine over a period of between 5 minutes and 75 minutes or more, preferably between 10 minutes and 45 minutes. It may be desirable to control the rate of combining the nitrile with the alcohol in order to ensure an optimum temperature is achieved. The reaction temperature may be between 10° C. and 60° C. It may be desirable to control the temperature such that it does not exceed 50° C. The reaction time may be over a period of at least 5 minutes and as long as 24 hours. Typically the reaction will be at least 5 minutes and often as much as 10 hours or more. At the end of the reaction it may be desirable to remove the excess acrylonitrile by conventional means, for example by evaporation under vacuum. Suitably the acrylonitrile may be removed under vacuum with a reduced pressure of between 15 mbar and 100 mbar at an elevated temperature of between 40° C. and 60° C. for a period of between 30 minutes and 60 minutes and optionally at an increased temperature of at least 65° C. and up to 85° C. Optionally it may be desirable to use a resin to remove any trace amounts of the nitrile. Desirably the resulting alkyl ether amino alkyl nitrile should have a purity of at least 55% and often at least 60%

In a second step of the process the nitrile group of the alkyl ether amino alkyl nitrile of step one is reduced to the corresponding amine. This can be achieved by any conventional process for the reduction of nitriles to amines. Desirably the alkyl ether amino alkyl nitrile should be reacted with hydrogen in the presence of a suitable catalyst. An example of suitable catalysts includes Raney-Cobalt. This may be carried out in the presence of a suitable aprotic solvent such as tetrahydrofuran.

Typically the reaction may be carried out at elevated temperatures, for instance at least 80° C., desirably at least 90° C., and possibly up to 140° C. or more. Preferably the reaction would be carried out at temperatures of between 100° C. and 130° C. In addition to elevated temperatures it may often be desirable to carry out process under increased pressure usually of at least 40 bar or more, for instance at least 45 bar. It may often be desirable to increase the pressure to even higher levels for instance up to 350 bar or higher, for instance between 250 bar and 300 bar. At the end of the reaction it may usually be desirable to remove the catalyst. This can be done by conventional filtration means.

Desirably the resulting alkyl ether diamine should have a purity of at least 55% and often at least 60% or higher.

In an alternative process for producing the aforementioned alkyl ether diamines the respective corresponding alkyl either amine can be reacted with a C2-6 alkylene oxide in a similar way described above for alkyl ether amines in order to produce the corresponding alkyl ether amino alcohol.

The compounds of formulae (IIIb) may conveniently be prepared by addition of an acidic compound to the corresponding alkyl ether diamines of formula (IIIa). The acid the compound will protonate the amine group and then the negatively charged acid radical will form the negatively charged $Y^-$ component. The acidic compound may be any suitable acid, for instance acids whose radicals are selected from the group consisting of carboxylate, sulphate, sulphonate, chloride, bromide, iodide, fluoride, nitrate, and phosphate. Preferably the acid is a carboxylic acid, particularly an aliphatic or olefinic carboxylic acid having between one and six carbon atoms. More preferably a carboxylic acid is an aliphatic carboxylic acid having between one and three carbon atoms i.e. formic acid, acetic acid or propionic acid. Acetic acid is preferred.

The acidic compound may be added in a molar equivalence to the corresponding alkyl ether diamine compound of formula (IIIa). It may be desirable to add a lesser amount of the acidic compound which will result in partial protonation and therefore result in a mixture of the respective protonated compound of formula (IIIb) and the corresponding alkyl ether diamine compound of formula (IIIa). It may also be desirable to add a greater amount of the acidic compound resulting in a stoichiometric excess of the acidic compound. Typically the ratio of acidic compound to alkyl ether diamine may be between 1:25 and 1.5:1, especially between 1:20 and 1:1.

The acidic compound may be added drop wise over a period of time between one minute and 45 minutes to the alkyl ether amine, for instance between five minutes and 30 minutes. The resulting compound of formula (IIIb) desirably will form as a homogenous solution which will remain clear and liquid during storage.

The present invention also relates to the use of at least one of the compounds of formulae (Ia) and/or (Ib) as flotation collectors for enriching an iron mineral from a silicate-containing iron ore.

In accordance with the present invention any of the compounds of formulae (Ia) or (Ib) provide improved results in enriching the iron material. Preference may be given to using a combination of these compounds. For instance an alkyl amido di-(alkyl ether amine) compound (Ia) may be used in combination with the corresponding protonated compound (Ib). The compounds of formulae (Ia) and/or (Ib) may also be used in conjunction with any of the aforementioned compounds (IIa) and/or (IIb) and/or (IIIa) and/or (IIIb) or combinations of these compounds.

The invention further relates to compositions suitable for use in enriching an iron mineral from a silicate-containing iron ore comprising of at least one of the compounds of formulae (Ia) and/or (Ib). Said compositions may additionally comprise any of compounds (IIa) and/or (IIb) and/or (IIIa) and/or (IIIb) or combinations thereof.

The use of said composition as collecting formulations for enriching an iron mineral from a silicate-containing iron ore is also claimed.

When the compounds of the invention or formulations containing them are used as collectors or in collector formulations in an inverse flotation process a much better selection removal of silicate is achieved by comparison to commercially available or other known alkyl ether amines or other known collectors. The present invention provides improved removal of silicate without suffering an increased loss of the iron mineral. In fact the collectors of the present invention enable a higher proportion of the iron to be retained and a higher proportion of the silicate to be removed.

In the process according to the invention for enriching an iron mineral from a silicate containing iron ore by inverse flotation conventional inverse flotation plant equipment may be used. In general the iron ore can be combined with water or suitable aqueous liquid and mixed using mechanical mixing means to form a homogenous slurry. The flotation process is normally carried out in one or more flotation cells. The collector would normally be introduced into the slurry in the flotation cell. Typically the collector will condition the dispersed iron ore of the slurry. A suitable period of conditioning will tend to be at least one minute and sometimes as much as 10 or 15 minutes. Following the conditioning period air would tend to be injected into the base of the flotation cell and the air bubbles so formed would tend to rise to the surface and generate a froth on the surface. The injection an air may be continued until no more froth is formed, which may be for at least one minute and as much as 15 or 20 minutes. The froth can be collected and removed. The residual slurry can be treated again in a similar manner at least once. In some cases it may be desirable to further treat the residual slurry again in a similar manner at least once for instance between 4 and 6 treatments. Nevertheless, it will generally be unnecessary to further treat the residual slurry again.

The flotation process may be performed in a conventional pH range. This may be in the range of between 5 and 12, such as 9 and 11. This tends to provide that the minerals would exhibit the correct surface charge.

A conventional depressing agent, such as a hydrophilic polysaccharide, may be used in a conventional quantity sufficient to cover the iron or surface in the requisite amount. Typically a suitable hydrophilic polysaccharide includes different kinds of starches.

It may also be desirable to include a froth regulator in the system in order to improve the efficiency. Nevertheless such froth regulators are not essential. Examples of conventional from regulators include methylisobutyl carbinol and alcohols having between six and 12 carbon atoms, such as ethylhexanol, and alkoxylated alcohols.

Further conventional additives may be included in the flotation system, such as pH regulating agents, co-collectors, and extender oils.

The typical ores of iron suitable for treatment according to the invention include haematite and magnetite ores. The invention is particularly suitable to haematite. Furthermore, the invention is suitable for processing of iron ores, for instance haematites containing high silica contents, for instance at least 20% by weight of iron ore, often at least 30%, and even at least 40% or more, for instance up to 60% or 70% or more.

The present invention is further illustrated by the following examples.

EXAMPLES

Synthesis

Following fatty acids have been transformed into corresponding alkyl amido ether diamines by reaction of fatty acid methyl ester with diethanolamine, followed by conversion with acrylonitrile and reduction of nitrile group to amino group. Compounds were optionally treated with acetic acid afterwards.

TABLE 1

| Fatty acid methyl ester | Description |
| --- | --- |
| Edenor 1270 ME | Product purchased from Cognis, mixture of dodecanoic and tetradecanoic acid methyl ester in an average ratio of 70:30 |
| Oleic acid methyl ester | Oleic acid methyl ester purchased from Aldrich |

Synthesis of C12C14 acid amido ether diamine:
a) Amidation

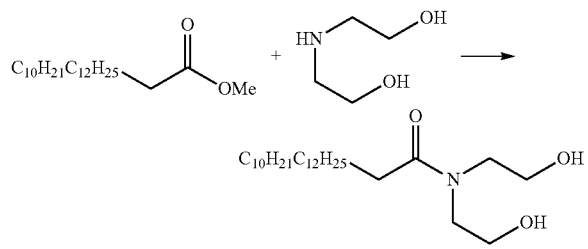

Edenor Me C1270 (224 g, 1 mol) was stirred in a 1 l round bottom flask under nitrogen stream (30 l/h) at 75° C. Diethanol amine (315 g, 3 mol) was added and phase separation occurred. Temperature was increased to 120° C. and first amount of MeOH was distilled off. Reaction became homogeneous and showed after 48 h stirring 70% conversion rate. Temperature was decreased to 90° C. and additional amount of diethanol amine (210 g, 2 mol) was added. After stirring for 60 h ester group signal in IR disappeared. Reaction was cooled down to 21° C., diluted with tert-butylmethylether (450 g) and extracted with diluted acetic acid (1% acetic acid in water, 4×300 g). After removal of tert-butylmethylether under vacuum the product was mixed with tetrahydrofuran and NaOMe solution (30% in MeOH, 13.3 g). After stirring for 10 min Ambosol was added (15 g), stirred for 30 min and filtrated (Seitz K 900). Product has been analyzed:
proton NMR (proton nmr in CDCl$_3$: δ=0.85, t, 3H (CH3), δ=1.2-1.65, m, 18.6H (CH2), δ=2.2-2.4, m, 2H (CH2CO), δ=2.5-2.9, m, 1H, δ=3.4-3.9, m, 7H) confirmed desired product, isolated signal of methyl ester could not be detected
GC showed signal of 7% which could be methyl ester
amin number was 0.19 mmol/g
acid number was 0.0095 mmol/g b) Addition

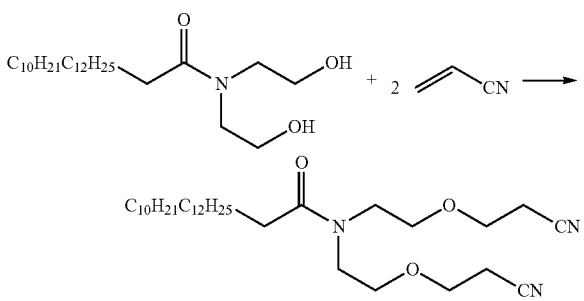

In a 1 l round bottom flask amidation product from above (149 g, 0.5 mol) was stirred with NaOMe (30% solution in MeOH, 0.75 g, 0.004 mol) in presence of tetrahydrofurane (181 g) at 21° C. Acrylonitrile (106 g, 2.0 mol) was added in such a way that temperature was kept below 50° C. Reaction was slow in the beginning, but showed exothermic behavior after some time. Temperature increased from 21° C. to 48° C. Reaction was stirred overnight. Excess of acrylonitrile was removed under vacuum (20 mbar) at 50° C. (and later at 75° C.) within 30 min. Ambosol (3 weight %) was added and mixture was filtrated (900 k Seitz filter).
Analytic showed following values:
proton NMR (proton nmr in CDCl$_3$: δ=0.85, t, 3H (CH3), δ=1.2-1.65, m, 18.6H (CH2), δ=2.35, m, 2H (CH2CO), δ=2.6, m, 4H (CH2CN), δ=3.5-3.75, m, 12H (CH2O, CH2NCO)) confirmed the structure and showed nearly complete conversion rate
7% of unknown compound according to GC are present c) Reduction

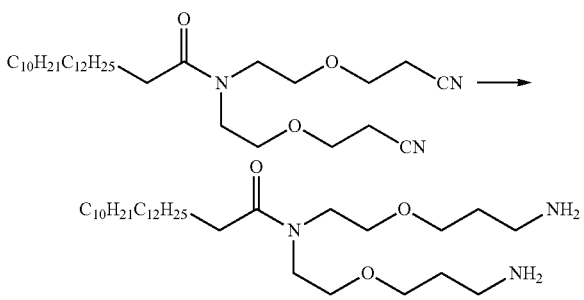

In a 300 ml autoclave tetrahydrofuran (15 g) was stirred with Raney-Cobalt (2 g), then flushed 3 times with nitrogen and stirred at 500 rpm. Hydrogen (12.8 l) was added until pressure reached 50 bar and reactor was heated to 120° C. During 60 min addition product from above (58.5 g, 0.145 mol; diluted with 10 ml THF) was added continuously (flow rate 1 ml/min). Pressure was increased to 72 bar. Additional hydrogen was added (28.3 l) until pressure of 280 bar was reached. Mixture was stirred for 35 h under these conditions. Pressure was kept at 280 bar (13.25 l were added). Reactor was cooled to room temperature and pressure gently released. Autoclave was flushed with nitrogen (10 bar). Catalyst was removed by filtration (Seitz K 900). According to amine titer, GC and proton NMR (proton nmr in CDCl$_3$: δ=δ=0.85, t, 3H (CH3), δ=1.2-1.65, m, 18.6H (CH2), δ=1.70, t, 2H (CH2), δ=1.90, t, 2H (CH2), δ=2.35, 2H (CH2CO), δ=2.75, t, 2H (CH2), δ=3.25, m, 2H (CH2), δ=3.4-3.6, m, 12H) following values were achieved:
- 4.8% un-reacted nitrile according to amine titer
- amide group survived conditions completely
- proton nmr confirmed structure
- no dimer formation observed.

d) Partial Protonation

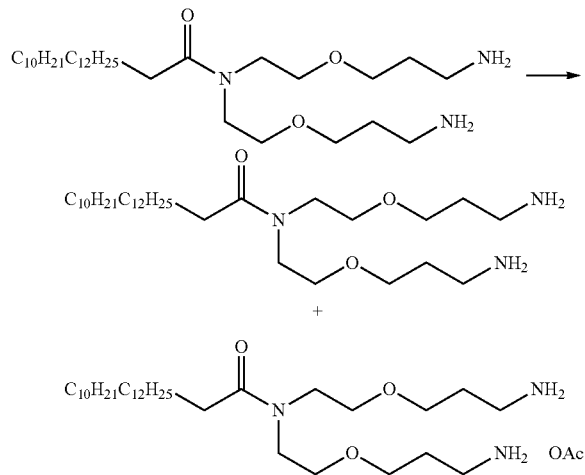

Reduction product from above (7 g, 0.017 mol,) was heated to 60° C. and stirred at this temperature. Acetic acid (0.05 g, 0.0009 mol) was added dropwise and stirred for another 10 min. Final product is a clear liquid.

The other samples were produced in similar way like C12C14 acid amido ether diamine.

Flotation Test

Following flotation protocol was applied for the different collectors.

500 g of dried iron ore (hematite) were poured in a 1 l flotation vessel of a lab flotation cell (MN 935/5, HUMBOLDT WEDAG). 1 l tab water was added and the resulting slurry was homogenized by stirring for two minutes (3000 rpm). 25 mL of a 1 weight % freshly prepared corn starch solution (=500 g/t ore) were mixed in. Subsequently, 25 μL of the liquid collector were injected (=50 g/t ore), pH was adjusted to 10 (with 50weight-% NaOH solution) and the slurry was conditioned for 5 minutes. The air flow was started (80 L/h) and the froth was collected until no stable froth was formed. The air flow was stopped and another 25 μL of collector were added and conditioned for 5 minutes, before the air flow was restarted. This procedure was repeated until five addition steps were carried out. The flotation froth of each step was dried, weighted and the obtained minerals characterized by elementary analysis via X-ray fluorescence (XRF).

For the tests two different hematite ores with different silica levels have been used.

TABLE 2

|  |  | pH | weight g | weight % | Fe | $Fe_{rec.}$ | $Fe_{rec}$ (Residue) | Si | $SiO_2$ | $SiO_2$ (Residue) | $SiO_2\ _{rec.}$ |
|---|---|---|---|---|---|---|---|---|---|---|---|
| Flotigam EDA | Froth 1 | 10.5 | 8 | 1.6% | 25.3% | 1.1% | 98.9% | 24.8% | 53.1% | 43.7% | 1.9% |
| iC12oxypropylamine + | Froth 2 | 10.4 | 51 | 10.1% | 15.8% | 4.3% | 94.7% | 34.4% | 73.6% | 40.3% | 17.0% |
| 50% acetic acid | Froth 3 | 10.3 | 57 | 11.3% | 10.2% | 3.1% | 91.6% | 38.7% | 82.8% | 34.0% | 21.3% |
| (Comparative | Froth 4 | 10.0 | 28 | 5.5% | 7.6% | 1.1% | 90.5% | 40.1% | 85.8% | 30.0% | 10.9% |
| monoamine) | Froth 5 | 9.9 | 42 | 8.3% | 9.3% | 2.1% | 88.4% | 39.3% | 84.1% | 22.9% | 16.0% |
|  | Residue | — | 319 | 63.2% | 52.3% | 88.4% |  | 10.7% | 22.9% |  | 33.0% |
|  | Total | — | 505 | 100.0% | 37.4% | 100.0% |  | 20.5% | 43.8% |  | 100.0% |
| Aerosurf MG-83 | Froth 1 | 10.3 | 63 | 12.5% | 9.9% | 3.2% | 96.8% | 38.8% | 83.0% | 38.4% | 23.5% |
| iC13oxypropyl-1,3- | Froth 2 | 10.2 | 151 | 29.9% | 11.4% | 8.9% | 87.8% | 38.1% | 81.5% | 16.1% | 55.4% |
| propan diamine + | Froth 3 | 9.5 | 31 | 6.1% | 18.7% | 3.0% | 84.8% | 32.6% | 69.7% | 9.7% | 9.7% |
| 5% acetic acid | Froth 4 | 9.4 | 51 | 10.1% | 51.3% | 13.6% | 71.3% | 11.7% | 25.0% | 5.9% | 5.7% |
| (Comparative | Froth 5 | 9.0 | 9 | 1.8% | 59.2% | 2.8% | 68.5% | 6.8% | 14.5% | 5.6% | 0.6% |
| diamine) | Residue | — | 200 | 39.6% | 66.1% | 68.5% |  | 2.6% | 5.6% |  | 5.0% |
|  | Total | — | 505 | 100.0% | 38.2% | 100.0% |  | 20.6% | 44.0% |  | 100.0% |
| Lilaflot D 817M | Froth 1 | 10.2 | 47 | 9.3% | 9.7% | 2.4% | 97.6% | 38.8% | 83.0% | 39.3% | 17.9% |
| iC12oxypropyl-1,3- | Froth 2 | 10.0 | 43 | 8.5% | 11.9% | 2.7% | 95.0% | 37.5% | 80.2% | 35.0% | 15.8% |
| propan diamine + | Froth 3 | 9.6 | 11 | 2.2% | 7.5% | 0.4% | 94.5% | 40.9% | 87.5% | 33.6% | 4.4% |
| 20-40 mol % | Froth 4 | 9.6 | 16 | 3.2% | 10.5% | 0.9% | 93.6% | 38.7% | 82.8% | 31.6% | 6.1% |
| acidic acid | Froth 5 | 9.5 | 16 | 3.2% | 16.5% | 1.4% | 92.3% | 34.6% | 74.0% | 29.7% | 5.4% |
| (Comparative | Residue | — | 371 | 73.6% | 47.7% | 92.3% |  | 13.9% | 29.7% |  | 50.5% |
| diamine) | Total | — | 504 | 100.0% | 38.1% | 100.0% |  | 20.3% | 43.4% |  | 100.0% |
| N,N Di-(6-Amino-3- | Froth 1 | 10.5 | 18 | 3.6% | 19.7% | 1.9% | 98.1% | 30.6% | 65.5% | 43.7% | 5.3% |
| oxyhexyl)dodecyl- | Froth 2 | 10.4 | 84 | 16.7% | 9.7% | 4.3% | 93.9% | 39.1% | 83.6% | 35.4% | 31.3% |
| amide + | Froth 3 | 10.0 | 63 | 12.5% | 6.7% | 2.2% | 91.7% | 41.4% | 88.6% | 25.5% | 24.9% |
| 20 mol % | Froth 4 | 9.9 | 36 | 7.1% | 8.2% | 1.5% | 90.1% | 40.4% | 86.4% | 18.3% | 13.9% |
| acidic acid | Froth 5 | 9.7 | 43 | 8.5% | 21.4% | 4.8% | 85.3% | 31.2% | 66.7% | 10.3% | 12.8% |
| (Product 1) | Residue | — | 260 | 51.6% | 62.6% | 85.3% |  | 4.8% | 10.3% |  | 11.9% |
|  | Total | — | 504 | 100.0% | 37.9% | 100.0% |  | 20.8% | 44.5% |  | 100.0% |
| N,N Di-(6-Amino-3- | Froth 1 | 10.4 | 0 | 0.0% | 0.0% | 0.0% | 100.0% | 0.0% | 0.0% | 43.7% | 0.0% |
| oxyhexyl)-9- | Froth 2 | 10.4 | 12 | 2.4% | 21.4% | 1.3% | 98.7% | 29.5% | 63.1% | 43.2% | 3.4% |
| octadecenylamide + | Froth 3 | 10.3 | 82 | 16.3% | 7.8% | 3.3% | 95.4% | 40.5% | 86.6% | 34.6% | 32.3% |

TABLE 2-continued

| | | pH | weight g | weight % | Fe | Fe$_{rec.}$ | Fe$_{rec}$ (Residue) | Si | SiO$_2$ | SiO$_2$ (Residue) | SiO$_{2\,rec.}$ |
|---|---|---|---|---|---|---|---|---|---|---|---|
| 5 mol % acidic acid (Product 2) | Froth 4 | 10.0 | 125 | 24.9% | 5.5% | 3.6% | 91.8% | 42.4% | 90.7% | 9.8% | 51.6% |
| | Froth 5 | 9.9 | 39 | 7.8% | 27.1% | 5.5% | 86.3% | 27.2% | 58.2% | 2.1% | 10.3% |
| | Residue | — | 245 | 48.7% | 68.1% | 86.3% | | 1.0% | 2.1% | | 2.4% |
| | Total | — | 503 | 100.0% | 38.4% | 100.0% | | 20.4% | 43.7% | | 100.0% |
| N,N Di-(6-Amino-3-oxyhexyl)-9-octadecenylamide + 20 mol % acidic acid (Product 3) | Froth 1 | 10.1 | 0 | 0.0% | 0.0% | 0.0% | 100.0% | 0.0% | 0.0% | 43.2% | 0.0% |
| | Froth 2 | 10.1 | 5 | 1.0% | 18.5% | 0.5% | 99.5% | 31.5% | 67.4% | 43.0% | 1.6% |
| | Froth 3 | 10.1 | 67 | 13.4% | 6.2% | 2.1% | 97.4% | 41.6% | 89.0% | 35.7% | 27.6% |
| | Froth 4 | 10.1 | 123 | 24.6% | 6.7% | 4.2% | 93.1% | 41.4% | 88.6% | 14.4% | 50.4% |
| | Froth 5 | 10.0 | 42 | 8.4% | 17.0% | 3.7% | 89.5% | 34.0% | 72.7% | 5.1% | 14.1% |
| | Residue | — | 263 | 52.6% | 66.0% | 89.5% | | 2.4% | 5.1% | | 6.3% |
| | Total | — | 500 | 100.0% | 38.8% | 100.0% | | 20.2% | 43.2% | | 100.0% |

As one can see in table 2 the claimed compounds deliver better results compared to the commercial products Flotigam, Aerosurf or Lilaflot. Commercial compounds lead to high contents of SiO2 (above 20%) in the residue. Once level is lower, then level of precious Fe is below 70%. Claimed compounds are much more selective for example, in the case of product 2 only 2.1% SiO$_2$ is in the residue while Fe content is at 86.3%.

TABLE 3

| | | pH | weight g | weight % | Fe | Fe$_{rec.}$ | Fe$_{rec}$ (Residue) | Si | SiO$_2$ | SiO$_2$ (Residue) | SiO$_{2\,rec.}$ |
|---|---|---|---|---|---|---|---|---|---|---|---|
| Flotigam EDA iC12oxypropylamine + 50% acetic acid (Comparative monoamine) | Froth 1 | 10.6 | 2 | 0.4% | 7.2% | 0.1% | 99.9% | 40.9% | 87.5% | 33.4% | 1.0% |
| | Froth 2 | 10.4 | 3 | 0.6% | 7.2% | 0.1% | 99.8% | 40.9% | 87.5% | 33.1% | 1.5% |
| | Froth 3 | 10.3 | 10 | 2.0% | 7.2% | 0.3% | 99.5% | 40.9% | 87.5% | 32.0% | 5.2% |
| | Froth 4 | 10.3 | 21 | 4.2% | 4.2% | 0.4% | 99.1% | 43.4% | 92.8% | 29.2% | 11.5% |
| | Froth 5 | 10.2 | 22 | 4.4% | 3.9% | 0.4% | 98.8% | 43.4% | 92.8% | 26.1% | 12.0% |
| | Residue | — | 447 | 88.5% | 50.4% | 98.8% | | 12.2% | 26.1% | | 68.7% |
| | Total | — | 505 | 100.0% | 45.2% | 100.0% | | 15.7% | 33.6% | | 100.0% |
| 25 wt % [1:1(C10-Guerbet-oxy-propylamine) + C12/14-oxy-propylamine) + 20 mol % acetic acid] 75 wt % [N,N Di-(6-Amino-3-oxyhexyl)-9-octadecenyl-amide + 40 mol % acetic acid] | Froth 1 | 10.3 | 10 | 2.0% | 13.3% | 0.6% | 99.4% | 36.0% | 77.0% | 33.4% | 4.5% |
| | Froth 2 | 10.2 | 58 | 11.6% | 4.8% | 1.2% | 98.2% | 42.8% | 91.6% | 25.6% | 31.1% |
| | Froth 3 | 9.6 | 83 | 16.7% | 4.3% | 1.6% | 96.6% | 43.2% | 92.4% | 9.6% | 44.9% |
| | Froth 4 | 9.6 | 30 | 6.0% | 13.9% | 1.9% | 94.7% | 36.2% | 77.4% | 3.1% | 13.6% |
| | Froth 5 | 9.5 | 17 | 3.4% | 51.2% | 3.9% | 90.9% | 11.5% | 24.6% | 1.9% | 2.5% |
| | Residue | — | 300 | 60.2% | 68.2% | 90.9% | | 0.9% | 1.9% | | 3.4% |
| | Total | — | 498 | 100.0% | 45.2% | 100.0% | | 16.0% | 34.3% | | 100.0% |
| 75 wt % [1:1(C10-Guerbet-oxy-propylamine) + C13/15-oxy-propylamine) + 5 mol % acetic acid] 25 wt % [N,N Di-(6-Amino-3-oxyhexyl)-9-octadecenyl-amide + 40 mol % acetic acid] | Froth 1 | 10.5 | 3 | 0.6% | 12.3% | 0.2% | 99.8% | 37.0% | 79.2% | 34.4% | 1.4% |
| | Froth 2 | 10.5 | 14 | 2.8% | 12.3% | 0.8% | 99.1% | 37.0% | 79.2% | 33.2% | 6.3% |
| | Froth 3 | 10.4 | 50 | 9.9% | 4.5% | 1.0% | 98.1% | 42.9% | 91.8% | 26.5% | 26.1% |
| | Froth 4 | 9.9 | 49 | 9.7% | 3.3% | 0.7% | 97.4% | 43.8% | 93.7% | 18.0% | 26.1% |
| | Froth 5 | 9.9 | 66 | 13.0% | 7.1% | 2.1% | 95.3% | 41.0% | 87.7% | 3.9% | 33.0% |
| | Residue | — | 324 | 64.0% | 66.6% | 95.3% | | 1.8% | 3.9% | | 7.1% |
| | Total | — | 506 | 100.0% | 44.7% | 100.0% | | 16.2% | 34.7% | | 100.0% |

As one can see in table 3 claimed formulations work better than commercial product like Flotigam. Rather low SiO2 level (~2-4%) are achieved while Fe content is above 90% in the residue.

The invention claimed is:

1. A process for enriching an iron mineral from a silicate comprising iron ore, the process comprising performing inverse flotation, by adding, to the iron ore, a collector or collector composition comprising at least one of the compounds of formulae

  (Ia) and

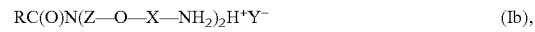  (Ib), wherein

X is an aliphatic alkylene group comprising 2 to 6 carbon atoms;

Z is an aliphatic alkylene group comprising 2 to 6 carbon atoms;

Y$^-$ is an anion; and

R is a saturated or unsaturated, linear or branched, aliphatic or aromatic hydrocarbyl moiety having between 7 and 23 carbon atoms.

2. The process according to claim 1, wherein R group is an unsaturated hydrocarbyl moiety.

3. The process according to claim 1, wherein X is an —CH$_2$CH$_2$CH$_2$— moiety and Z is a linear or branched alkylene group.

4. The process according to claim 1, wherein Y$^-$ is CH$_3$CO$_2{}^-$.

5. The process according to claim 1, wherein the collector or collector composition comprises, in conjunction with at least one of the compounds of formulae (Ia) and (Ib), compounds of formulae R'O—CH$_2$CH$_2$CH$_2$—NH$_2$ (IIa) and R'O—CH$_2$CH$_2$CH$_2$—NH$_3{}^+$Y$^-$ (IIb), wherein R' is a linear or branched hydrocarbyl group of between 8 and 18 carbon atoms.

6. The process according to claim 1, wherein the collector or collector composition comprises, in conjunction with at least one of the compounds of formulae (Ia) and (Ib), compounds of formulae R'O—CH$_2$CH$_2$CH$_2$—NH—CH$_2$CH$_2$CH$_2$—NH$_2$ (IIIa) and R'O—CH$_2$CH$_2$CH$_2$—NH—CH$_2$CH$_2$CH$_2$—NH$_3{}^+$Y$^-$ (IIIb), wherein R' is a linear or branched hydrocarbyl group of between 8 and 18 carbon atoms.

7. The process according to claim 1, wherein the collector or collector composition comprises, in conjunction with at least one of the compounds of formulae (Ia) and (Ib), compounds of formulae R'O—CH$_2$CH$_2$CH$_2$—NH$_2$ (IIa) and R'O—CH$_2$CH$_2$CH$_2$—NH$_3{}^+$Y$^-$ (IIb), together with compounds of formulae R'O—CH$_2$CH$_2$CH$_2$—NH—CH$_2$CH$_2$CH$_2$—NH$_2$, (IIIa) and R'O—CH$_2$CH$_2$CH$_2$—NH—CH$_2$CH$_2$CH$_2$—NH$_3{}^+$Y$^-$ (IIIb)

wherein R' is a linear or branched hydrocarbyl group of between 8 and 18 carbon atoms.

8. The process according to claim 1, wherein the process comprises performing froth flotation.

9. The process according to claim 1, further comprising employing an additional frother.

10. The process according to claim 1, wherein the iron ore is haematite.

11. The process according to claim 1, further comprising adding a depressant.

12. A compound of formulae:

RC(O)N(Z—O—X—NH$_2$)$_2$ (Ia); or

RC(O)N(Z—O—X—NH$_2$)$_2$H$^+$Y$^-$ (Ib), wherein
X is an aliphatic alkylene group comprising 2 to 6 carbon atoms,
Z is an aliphatic alkylene group comprising 2 to 6 carbon atoms,
Y$^-$ is an anion, and
R is a saturated or unsaturated, linear or branched, aliphatic or aromatic hydrocarbyl moiety having between 7 and 23 carbon atoms.

13. A composition suitable for enriching an iron mineral from a silicate comprising iron ore comprising at least one of the compounds of formulae (Ia) and (Ib) according to claim 12.

14. The compound according to claim 12, wherein the compound is a flotation collector in enriching an iron material from a silicate comprising iron ore.

15. A method for preparing a compound of formula:

RC(O)N(Z—O—X—NH$_2$)$_2$ (Ia)

according to claim 12,
the method comprising, in the following order:
reacting a carboxylic acid ester RC(O)—OM with a dialkanolamine HN(Z—OH)$_2$ to form an alkyl amido dialkanol RC(O)—N(Z—OH)$_2$ in which M is an alkyl group;
reacting the alkyl amido dialkanol with an ethylenically unsaturated nitrile comprising 3 to 6 carbon atoms to form an alkyl amido di-(alkyl ether nitrile) RC(O)—N(Z—O—X≡N)$_2$; and
reducing the alkyl amido di-(alkyl ether nitrile) to form the compound of formula (Ia).

16. A method for preparing a compound of formula:

RC(O)N(Z—O—X—NH$_2$)$_2$H$^+$Y$^-$ (Ib)

according to claim 12,
the method comprising reacting a compound of formula RC(O)N(Z—O—X—NH$_2$)$_2$ with an acidic compound HY to form the compound of formula (Ib).

17. The process according to claim 3, wherein Z is a —CH$_2$CH$_2$ moiety.

18. The process according to claim 5, wherein R' is a branched hydrocarbyl group of between 10 and 15 carbon atoms.

19. The process according to claim 6, wherein R' is a branched hydrocarbyl group of between 10 and 15 carbon atoms.

20. The process according to claim 9, wherein the additional frother is at least one selected from the group consisting of a branched aliphatic alcohol with 10 or less carbon atoms, a polyalkoxylate, and an alkyl ethoxylate.

* * * * *